US012778880B2

(12) United States Patent
Sappapan

(10) Patent No.: US 12,778,880 B2
(45) Date of Patent: Nov. 3, 2026

(54) SKINCARE COMPOSITION CONTAINING SHATAVARI EXTRACT

(71) Applicant: Bangkok Lab and Cosmetic Public Company Limited, Ratchaburi (TH)

(72) Inventor: Ruengrit Sappapan, Bangkok (TH)

(73) Assignee: BANGKOK LAB AND COSMETIC PUBLIC COMPANY LIMITED, Ratchaburi (TH)

( * ) Notice: Subject to any disclaimer, the term of this patent is extended or adjusted under 35 U.S.C. 154(b) by 364 days.

(21) Appl. No.: 18/468,697

(22) Filed: Sep. 16, 2023

(65) Prior Publication Data

US 2024/0398694 A1 Dec. 5, 2024

(30) Foreign Application Priority Data

Jun. 2, 2023 (TH) ................................ 2301003362

(51) Int. Cl.

| | |
|---|---|
| ***A61K 8/9794*** | (2017.01) |
| ***A61K 8/42*** | (2006.01) |
| ***A61K 8/44*** | (2006.01) |
| ***A61K 8/73*** | (2006.01) |
| ***A61Q 19/08*** | (2006.01) |

(52) U.S. Cl.

CPC .............. *A61K 8/9794* (2017.08); *A61K 8/42* (2013.01); *A61K 8/44* (2013.01); *A61K 8/735* (2013.01); *A61Q 19/08* (2013.01); *A61K 2800/524* (2013.01)

(58) Field of Classification Search

CPC .......... A61K 8/9794; A61K 8/42; A61K 8/44; A61K 8/735; A61K 2800/524; A61K 8/365; A61K 8/9789; A61Q 19/08; A61Q 19/00

See application file for complete search history.

(56) References Cited

U.S. PATENT DOCUMENTS 5,693,327 A 12/1997 Shah

FOREIGN PATENT DOCUMENTS

| | | | | |
|---|---|---|---|---|
| EP | 2248526 | A1 * | 11/2010 | .......... A61K 36/185 |
| JP | 1192332 | A | 4/1999 | |
| JP | 2010159213 | A | 7/2010 | |
| TH | 20550 | A | 12/2022 | |
| WO | 20100086724 | A2 | 8/2010 | |
| WO | 20100086724 | A3 | 8/2010 | |
| WO | 20101064172 | A2 | 9/2010 | |
| WO | 20101064172 | A3 | 9/2010 | |

OTHER PUBLICATIONS

Singh, A.K., et al. Phytochemicals, Medicinal and Food Applications of Shatavari (*Asparagus racemosus*): An Updated Review. 2018. The Nat Prod J, 8:32-44, 13 pages. DOI: 10.2174/2210315507666170922145258. (Year: 2018).*

Potduang, B., et al. Biological activities of Asparagus racemosus. Afr J Tradit Complement Altern Med. 2008, 5(3):230-7, Erratum 2010, 7(4):377, 8 pages. doi: 10.4314/ajtcam.v5i3.31278. PMID: 20161942; PMCID: PMC2816549. (Year: 2010).*

Teich, J. The Skincare Dictionary: Every Ingredient Explained. Good Housekeeping. 2021, 17 pages. <https://www.goodhousekeeping.com/beauty/anti-aging/a34102257/skincare-ingredient-dictionary/>. (Year: 2021).*

Meckfessel MH & Brandt S. The structure, function, and importance of ceramides in skin and their use as therapeutic agents in skin-care products. J Am Acad Dermatol. 2014, 71(1):177-84, 8 pages. doi: 10.1016/j.jaad.2014.01.891. Epub Mar. 20, 2014. PMID: 24656726. (Year: 2014).*

Maylis, The different types of hyaluronic acid in skincare, 2022, Typology, 6 pages. <https://web.archive.org/web/20230203105755/https://us.typology.com/library/the-different-types-of-hyaluronic-acid-in-skincare>. (Year: 2022).*

Special Chem, Disodium EDTA, 2022, 7 pages. <https://www.specialchem.com/cosmetics/inci-ingredients/disodium-edta>. (Year: 2022).*

Dréno, B., et al. Safety review of phenoxyethanol when used as a preservative in cosmetics. J Eur Acad Dermatol Venereol. Nov. 2019; 33 Suppl 7:15-24, 10 pages. doi: 10.1111/jdv.15944. PMID: 31588615. (Year: 2019).*

Fleur & Bee, Carbomer for skin: benefits, how to use, 2022, 11 pages. <https://fleurandbee.com/blogs/news/carbomer-for-skin>. (Year: 2022).*

(Continued)

*Primary Examiner* — Aaron J Kosar
*Assistant Examiner* — Jennifer Lynn Cain
(74) *Attorney, Agent, or Firm* — SALIWANCHIK, LLOYD & EISENSCHENK

(57) ABSTRACT

The skincare composition contains Shatavari extract according to this invention. The composition comprises a particular amount of Shatavari extract that is effective in stimulating estrogen receptor, inhibiting 5α-reductase, inhibiting tyrosinase, and is non-cytotoxic. The said composition contains only essential ingredients that do not interfere with the absorption of active ingredients and cause no irritation. In one embodiment, the skincare gel comprises edetate disodium, high molecular weight hyaluronic acid, medium molecular weight hyaluronic acid, low molecular weight hyaluronic acid, niacinamide, Shatavari extract, 2-phenoxyethanol, carbomer, lactic acid, and water.

12 Claims, 7 Drawing Sheets

(56) References Cited

OTHER PUBLICATIONS

Ruksiriwanich, W., et al. In Vitro and In Vivo Regulation of SRD5A mRNA Expression of Supercritical Carbon Dioxide Extract from Asparagus racemosus Willd. Root as Anti-Sebum and Pore-Minimizing Active Ingredients. Molecules. Feb. 24, 2022;27(5):1535, 16 pages. doi: 10.3390/molecules27051535. (Year: 2022).*

Liu X, et al. Improving solubility of poorly water-soluble drugs by protein-based strategy: A review. Int J Pharm. Mar. 5, 2023;634: 122704. doi: 10.1016/j.ijpharm.2023.122704, 15 pages. Epub Feb. 7, 2023. PMID: 36758883. (Year: 2023).*

Al-Niaimi, F., et al. “Topical vitamin C and the skin: mechanisms of action and clinical applications.” The Journal of clinical and aesthetic dermatology 10.7 (2017): 14-17.

Telang, P. S. “Vitamin C in dermatology.” Indian dermatology online journal 4.2 (2013): 143-146.

* cited by examiner 700 bp
5α-reductase

SKINCARE COMPOSITION CONTAINING SHATAVARI EXTRACT

CROSS REFERENCE TO RELATED APPLICATIONS

This application claims priority to Thailand application Ser. No. 2301003362, filed Jun. 2, 2023, which is incorporated herein by reference in its entirety.

TECHNICAL FIELD OF THE INVENTION

The present invention relates to cosmetic science in respect of the skincare composition containing Shatavari extract.

BACKGROUND OF THE INVENTION

Shatavari (or rak sam sib in Thai) is a scientific name for *Asparagus racemosus* Willd., which literally means the woman who possesses a hundred of husbands. This plant is the climber that wrapped around the other plants with spikes. Its roots are underground, similar to fingerroot. This plant is one of the succulents that are distributed in Thailand, India, Sri Lanka, Java, China, Malaysia, and Australia.

Rasayana, the science of youth and femininity in Ayurvedic scriptures, has been using Shatavari for over 3,000 years for youth, nourishing the womb and milk of mothers, and nourishing the body and skin of women. Pharmacological data showed that substances found in the roots are isoflavones and steroidal saponins, which have estrogen-like effects. Therefore, it plays a role in making the skin firm and moisturized, reducing wrinkles, slowing down aging, inhibiting 5α-reductase, controlling the face skin's oiliness, stimulating hair growth, and inhibiting tyrosinase for reducing blemishes, removing dark spots, and making the skin bright.

Natural vitamin C, in the form of L-ascorbic acid, has high antioxidant activity. In dermatology, it is used to prevent and treat skin aging caused by light. It is also used to treat dark skin conditions. It was found that applying 10% vitamin C could reduce the skin's redness from UVB exposure by 52% and sunburn by 40-60% and promote collagen production. The efficiency of vitamin C is 4 times higher when used in combination with vitamin E. It was found that the skincare formulation containing 15% vitamin C, 0.5% ferulic acid, and 1% vitamin E had 8 times higher efficiency. However, light affects the stability of natural vitamin C. Therefore, vitamin C, in the form of magnesium ascorbyl phosphate, is used. The effectiveness of antioxidant activity, skin protection from light, and stimulation of collagen production were reported in Telang P. S. 2013. Vitamin C in dermatology. *Indian Dermatol Online J.* 4 (2): 143-6. However, Al-Niaimi F. and Chiang N. Y. Z. 2017. Topical vitamin C and the skin: Mechanisms of action and clinical applications. *J Clin Aesthet Dermatol.* 10 (7): 14-7 disclosed that magnesium ascorbyl phosphate or the other forms of vitamin C did not increase L-ascorbic in the skin. In the double-blinded test of placebo and 10% vitamin C controlled groups of 10 volunteers, they further reported a statistically significant difference in reducing skin aging caused by light and reducing wrinkles. In another double-blinded test of placebo and 5% vitamin C controlled groups of 20 volunteers, they also found a statistically significant difference in reducing wrinkles.

At present, there are patents, petty patents, and patent applications in Thailand and internationally related to the skincare composition containing Shatavari extract, as follows:

International Patent Application No. WO2010086724A3, titled "Herbal cream and lotion compositions and methods of preparation thereof," disclosed the herbal cream and lotion comprising the herbal extract prepared by employing a supercritical fluid extraction or water extraction, essential oils, pharmaceutically acceptable excipients, and methods of preparation thereof, in which the extract is selected from Shatavari, 0.0001-0.5%.

International Patent Application No. WO2010106417A3, titled "Herbal personal care formulations and method of preparing the same," disclosed ingredients comprising herbal extract employing supercritical fluid extraction or water extraction, enzymes, essential oil, cosmeceutically acceptable excipients, and methods of preparing the same, of which various herbal extracts are of 0.5-2%, and the extract is selected from Shatavari.

Japanese Patent Application No. JPH1192332A, titled "Skin preparation composition for external use," disclosed a cosmetic composition or cosmeceutical capable of sustaining a moisture-retaining effect and reducing g dermatitis, in which comprises the extract of *Asparagus africanasua* and/or *Kigelia africana*, greater than or equal to 0.1% of dry weight.

Japanese Patent No. JP2010159213A, titled "Antioxidant," disclosed an antioxidant, an anti-oxidizing external preparation for skins, and an anti-oxidizing cosmetic that contains the extract of one or more plants. The extract can be selected from *Ficus benghalensis, Asparagus racemosus, Achyranthes aspera, Lawsonia alba*, and *Plumbago zeylanica.*

European Patent Application No. EP2248526A1 (Withdrawn), titled "Compositions containing an extract of asparagus and use thereof," disclosed a cosmetic composition or cosmeceutical for treating acne and reducing the appearance of oil or pores on the skin that contains Shatavari extract.

U.S. Pat. No. 5,693,327A (Expired), titled "Herbal compositions," disclosed a composition for the treatment. The composition comprises *Melia azadirachta* and/or *Centratherum anthelminthicum*, which further comprises *Asparagus racemosus.*

Due to the limitations of the unknown amount of the active Shatavari extract that binds to the epidermal estrogen receptor, inhibits tyrosinase, inhibits 5α-reductase, and is non-cytotoxic, which would not be apparent easily to the person skilled in the art in this field, the analyses as in drug research are required. In order to obtain the extract concentrations suitable for the formulations, various human cell types were cultured, such as human skin cells, prostate cancer cells, and breast cancer cells, and then cells, enzymes, and the expression of related genes were tested with the extract at various concentrations. The inventor has tested pharmacological effects and found that Shatavari extract has a very potent activity in stimulating estrogen hormone receptors at concentrations from 0.0001 (10,000-fold dilution) and up to a concentration of 0.001 (1,000-fold dilution), as well as inhibiting 5α-reductase. The non-cytotoxic concentrations start at 10,000 μg/mL, and the highest concentration is 10 μg/ml. It also inhibits tyrosinase, but inhibits collagenase activity only 0.03 times that of vitamin C. When considering the existing commercial products, there are products containing 15% vitamin C, 0.5% ferulic acid, and 1% vitamin E. As vitamin E is dissolved in oil, it is not suitable for water-based cosmetic formulations that focus on facial oil control. Thus, the inventors developed more efficient cosmetic formulations to change from ordinary cosmetics to cosmeceuticals, which have therapeutic effects. By adding Shatavari extract, the activity becomes more specific and is non-cytotoxic. In one embodiment, the formulation might further comprise L-ascorbic acid, a particular form of vitamin C, but in a smaller amount than is used in commercial products. The vitamin C in this invention is 1-4%, which is lower than the products on the market that have been used for a long time, causing it to be believed in the cosmetic industry that there must be 10-15% of vitamin C in the formulation in order to provide the best performance. Previous studies have tested the efficacy of vitamin C on the skin of volunteers; however, this invention tested the efficacy of vitamin C on cultured human skin cells under conditions in which environmental factors were controlled and the measurement accuracy was higher. In comparison, the amount of vitamin C in this invention is 2-7.5 times less than that of other products on the market. Besides reducing the cost of raw materials, this also solved the technical problem of the solubility of vitamin C in formulations containing Shatavari extract and/or niacinamide, which allows the product to contain more active ingredients than high-vitamin C products alone. Previously, this formulation could not be formulated successfully by using high amounts of vitamin C. In addition, high doses of vitamin C also cause irritation. This invention claims the formulation contains a small amount of Shatavari extract, only 0.01-2%. Unexpectedly, the amount of Shatavari extract, smaller than that of the previous invention, was shown to be effective in stimulating the growth of breast cancer cells, which is representative of estrogenic activity studies. It was also 767,358.626 times better than the standard β-estradiol. These results were calculated from Shatavari extract at a concentration of 0.001 (diluted 1,000 times), causing breast cancer cell survival to be the highest by 139.70%, compared to the standard substance at a concentration of 1,000 times, which could make breast cancer cell survival the highest at only 107.2%. Therefore, the determination of Shatavari extract content in this invention can produce an effective formulation, according to research. Shatavari extract's binding to estrogen receptors in such particular amounts results in stimulating the growth of epidermal cells. This makes skin cells firm and plump again. In addition, it has an inhibitory effect on 5α-reductase, which directly affects hair loss and the amount of oil produced by the sebaceous glands around the hair follicle. It also inhibits tyrosinase, thereby affecting the proliferation and inhibition of melanin production, resulting in bright skin, and reducing blemishes and dark spots.

SUMMARY OF THE INVENTION

The skincare composition of this invention contains particular amounts of Shatavari extract. These particular amounts were tested on human skin cells, prostate cancer cells, and breast cancer cells for enzymes and gene expression and showed that they are effective in stimulating estrogen receptor, and inhibiting 5α-reductase and tyrosinase. This converts the dose applied to the cells to be suitable for skin application pharmaceutically. The composition contains only a few essential substances; therefore, it does not interfere with the absorption of active ingredients and cause no irritation. In one embodiment, a skincare gel comprises edetate disodium, high molecular weight hyaluronic acid, medium molecular weight hyaluronic acid, low molecular weight hyaluronic acid, niacinamide, Shatavari extract, 2-phenoxyethanol, carbomer, lactic acid, and water. The uses of Shatavari extract in said particular amounts also include using fewer ingredients, resulting in decreased production costs and easier production.

DETAILED DESCRIPTION OF THE INVENTION

Figure 1:
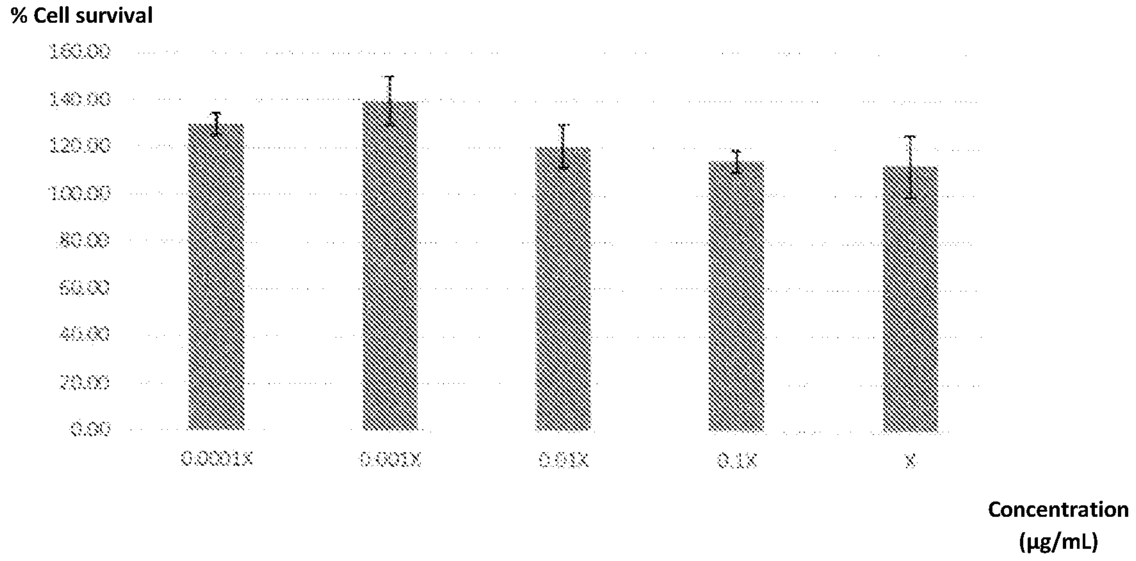
FIG. 1 shows % survival of breast cancer cells and Shatavari extract.

The skincare composition containing Shatavari extract for preparation of the product used with the body, scalp, or skin; particularly, skincare products for binding to the epidermal estrogen receptor, inhibiting tyrosinase, and/or inhibiting 5α-reductase, in a form selected from the group consisting of gels, essences, lotions, sprays, essences for masks, or scalp tonics. Said skincare composition comprises:

| | | |
|---|---|---|
| niacinamide | 0.3-3.5 | grams; |
| Shatavari extract | 0.01-2 | grams; |
| water q.s. to | 100 | grams. |

This invention further comprises:

| | | |
|---|---|---|
| chelating agent | 0.01-0.1 | grams; |
| moisturizer | 0.3-15 | grams; |
| preservative | 0.12-2 | grams; |
| pH-adjusting agent to pH 5.5-7.0. | | |

This invention also discloses suitable amounts of the ingredient, which is 0.6-2 grams of Shatavari extract, wherein Shatavari extracted by co-solvent between ethanol and supercritical carbon dioxide is preferred. Moreover, 95-97% ethanol is used, and/or Shatavari is extracted by 70% ethanol mixed with the surfactant according to the method of Thai Petty Patent No. 20550.

This invention will be described in detail hereafter.

The chelating agent is selected from any one of edetate disodium, ethylenediaminetetraacetic acid, ethylenediaminetetraacetic acid metal salts, or a combination thereof.

The moisturizer is selected from any one of hyaluronic acid, high molecular weight hyaluronic acid (higher than 1,800,000 Da), medium molecular weight hyaluronic acid (1,000,000-1,800,000 Da), low molecular weight hyaluronic acid (400,000-1,000,000 Da), hyaluronic acid S (100,000-400,000 Da), aloe vera gel (powder), nutto gum, hydrolyzed protein, urea, amino acid, cholesterol, sodium L-pyroglutamate, sodium lactate, propane-1,2,3-triol, or a combination thereof.

The preservative is selected from any one of benzyl alcohol; benzoic acid, or salts, or esters thereof; propionic acid, or salts thereof; salicylic acid, or salts thereof; sorbic acid, or salts thereof; o-phenylphenol, or salts thereof; 4-hydroxybenzoic acid, or methyl-, ethyl-, esters, and salts thereof; undec-10-enoic acid, or salts thereof; benzyl alcohol; 2-phenoxyethanol; 3-(2-ethylhexyloxy)propane-1,2-diol; methyl paraben; propyl paraben; methyl parahydroxybenzoate; propyl parahydroxybenzoate; 2-bromo-2-nitropropane-1,3-diol; imidazolidinyl urea; methylisothiazolinone; ethylenediaminetetraacetic acid; methyl paraben; propyl paraben; or a combination thereof. Salts mean sodium, potassium, calcium, magnesium, ammonium, and ethanolamine salts/chloride, bromide, sulphate, and acetate salts.

Esters mean the ester of methyl, ethyl, propyl, isopropyl, butyl, isobutyl, and phenyl.

This invention may further comprise the following:

Gelling agent selected from any one of carbomer, xanthan gum, arabic gum, carrageenan, cellulose, synthetic cellulose, mucilage in okra, or a combination thereof.

This invention also provides examples that can be easily understood by a person of ordinary skill in the art, but it is not limited by said examples.

Example 1

A soothing skincare gel comprises:

| | |
|---|---|
| edetate disodium | 0.01-0.05 grams; |
| high molecular weight hyaluronic acid | 0.05-0.15 grams; |
| medium molecular weight hyaluronic acid | 0.05-0.20 grams; |
| low molecular weight hyaluronic acid | 0.05-0.15 grams; |
| niacinamide | 1-2 grams; |
| Shatavari extract | 1-2 grams; |
| 2-phenoxyethanol | 1 grams; |
| carbomer | 0.18-0.56 grams; |
| lactic acid adjusted pH to pH 5.5; and | |
| water q.s. to | 100 grams. |

This invention further comprises the production method of the soothing skincare gel composition according to Example 1. The method comprises the following steps: adding edetate disodium into water; stirring until dissolved; adding high molecular weight hyaluronic acid, medium molecular weight hyaluronic acid, low molecular weight hyaluronic acid, niacinamide, Shatavari extract, and 2-phenoxyethanol into the solution; stirring until dissolved; keeping the reaction until used; adding carbomer into the solution; mixing thoroughly; adjusting pH with a lactic acid solution to 5.5.

This invention may further comprise panthenol, L-ascorbic acid (1-4 grams), ferulic acid.

Example 2

A skin brightening and nourishing essence comprises:

| | |
|---|---|
| edetate disodium | 0.02-0.03 grams; |
| high molecular weight hyaluronic acid | 0.1-0.2 grams; |
| medium molecular weight hyaluronic acid | 0.1-0.2 grams; |
| low molecular weight hyaluronic acid | 0.1-0.2 grams; |
| niacinamide | 1-2 grams; |
| Shatavari extract | 0.6-2.0 grams; |
| 2-phenoxyethanol | 1 grams; |
| carbomer | 0.2-0.5 grams; |
| L-ascorbic acid | 1-4 grams; |
| ferulic acid | 0.1-0.5 grams; |
| propan-1,2,3-triol | 0.1 grams; |
| lactic acid adjusted pH to pH 5.5; and | |
| water q.s. to | 100 grams. |

Example 3

A skin-moisturizing spray comprises:

| | |
|---|---|
| edetate disodium | 0.01 grams; |
| aloe vera gel (powder) | 0.1 grams; |
| urea | 1 grams; |
| hyaluronic acid S | 0.2 grams; |
| niacinamide | 1.8 grams; |
| Shatavari extract | 0.05 grams; |
| 2-phenoxyethanol | 1 grams; |
| lactic acid adjusted pH to pH 5.5; and | |
| water q.s. to | 100 grams. |

Example 4

An essence for masks comprises:

| | |
|---|---|
| edetate disodium | 0.01 grams; |
| medium molecular weight hyaluronic acid | 0.2 grams; |
| amino acid | 0.1 grams; |
| niacinamide | 2 grams; |
| Shatavari extract | 0.6 grams; |
| benzyl alcohol | 1 grams; |
| lactic acid adjusted pH to pH 5.5; and | |
| water q.s. to | 100 grams. |

Example 5

A scalp tonic product for reducing hair loss comprises:

| | |
|---|---|
| edetate disodium | 0.01 grams; |
| high molecular weight hyaluronic acid | 0.1 grams; |
| medium molecular weight hyaluronic acid | 0.1 grams; |
| low molecular weight hyaluronic acid | 0.1 grams; |
| niacinamide | 1.5 grams; |
| panthenol | 0.5 grams; |
| Shatavari extract | 1.2 grams; |
| benzyl alcohol | 1 grams; |
| triethanolamine adjusted pH to pH 6.0-6.5; and | |
| water q.s. to | 100 grams. |

This invention will be described in detail hereafter. The production method of products containing the composition according to Examples 2-5 is similar to the disclosed production method of the soothing skincare gel composition according to Example 1. Different preservatives may be used, and the pH value may be different; however, the production method is the same. The different ingredients, such as panthenol, L-ascorbic acid, ferulic acid, and propane-1,2,3-triol, are mixed in the same step as niacinamide.

This invention may further comprise the following:

A cosmetic wax is selected from any one of shea butter, mango wax, avocado wax, cupuacu butter, coconut wax, cacao wax, petrolatum, beeswax, stearyl alcohol, cetyl alcohol, or a combination thereof.

A substitute for beeswax, an emulsifying wax, is ceteareth-20, candelilla wax, cetearyl alcohol, carnauba wax, or soy wax.

A cosmetic oil is selected from any one of flaxseed oil, jojoba oil, rosehip oil, avocado oil, perilla oil, Sacha Inchi oil, coconut oil, caprylic or capric triglyceride, sunflower seed oil, castor oil, olive oil, carrot seed oil, argan oil, tea seed oil, or a combination thereof.

A ceramide is selected from any one of ceramide 1, ceramide 1A, ceramide 2, ceramide 3, ceramide 6, ceramide 6 II, ceramide AP, ceramide AS, ceramide EOP, ceramide EOS, ceramide NP, ceramide NS, or a combination thereof.

An emulsifier is selected from any one of propane-1,2,3-triol, hydrogenated lecithin, polyoxyethylene 20 sorbitan monooleate, polyoxyethylene 23 dodecanol, triethanolamine, or a combination thereof.

This invention also provides examples that can be very easily understood by a person of ordinary skill in the art, but it is not limited by said examples.

Example 6

A concentrated, nourishing skin lotion for combating skin allergies and dry itching comprises:

| | |
|---|---|
| edetate disodium | 0.05 grams; |
| sodium lactate | 1-2 grams; |
| sodium L-pyroglutamate | 0.5-2 grams; |
| urea | 5-8 grams; |
| niacinamide | 2 grams; |
| Shatavari extract | 2 grams; |
| shea butter | 20 grams; |
| flaxseed oil | 5 grams; |
| jojoba oil | 5 grams; |
| hydrogenated lecithin | 4 grams; |
| ceramide 1 | 0.2 grams; |
| ceramide 2 | 0.2 grams; |
| ceramide 3 | 0.2 grams; |
| α-tocopherol | 0.01 grams; |
| benzyl alcohol | 1 grams; |
| lactic acid adjusted pH to pH 5.7; and | |
| water q.s. to | 100 grams. |

This invention further discloses the production method of concentrated nourishing skin lotion for combating skin allergies and dry itching, containing the composition according to Example 6. The method comprises the following steps: adding edetate disodium into water; stirring until dissolved; adding high molecular weight hyaluronic acid, medium molecular weight hyaluronic acid, low molecular weight hyaluronic acid, niacinamide, Shatavari extract, and benzyl alcohol; stirring until dissolved; keeping the reaction until used; heating the solid ingredient, which is shea butter, at a temperature of 70-90° C. until melted; adding the oil ingredients, including hydrogenated lecithin, flaxseed oil, and jojoba oil; when it cooled down, yet in a liquid state, adding ceramide 1, ceramide 2, ceramide 3, and α-tocopherol into the reaction; mixing thoroughly; adding the water phase kept previously; adjusting pH; storing at a temperature of 8-20° C. until solidification and stirring with a blender until a fluffy texture is formed.

Example 7

A soothing, moisturizing, anti-oxidant, skin-nourishing lotion comprises:

| | |
|---|---|
| edetate disodium | 0.05 grams; |
| propan-1,2,3-triol | 2-4 grams; |
| niacinamide | 2 grams; |
| Shatavari extract | 1 grams; |
| shea butter | 3 grams; |
| flaxseed oil | 5 grams; |
| hydrogenated lecithin | 0.5 grams; |
| polyoxyethylene 20 sorbitan monooleate | 0.5 grams; |
| xanthan gum | 0.3-0.5 grams; |
| ceramide 1 | 0.2 grams; |
| ceramide 2 | 0.2 grams; |
| ceramide 3 | 0.2 grams; |
| α-tocopherol | 0.05-0.1 grams; |
| 2-phenoxyethanol | 1 grams; |
| pH-adjusting agent to pH 6.0; and | |
| water q.s. to | 100 grams. |

Chemical Definitions

Glycerin (or glycerine), or glycerol, is a name according to the International Nomenclature for Cosmetic Ingredients, or INCI. Propane-1,2,3-triol is a name according to the International Union of Pure and Applied Chemistry, or IUPAC.

Caprylic or capric triglyceride is the universal name of a cosmetic ingredient. It is made of coconut oil processed by lipid and water separation (fractionated coconut oil). Its trademark name is Myristol 318.

A pH-adjusting agent includes triethanolamine, lactic acid, glycolic acid, and citric acid. Lactic acid is preferred.

The use of the composition according to this invention is for product preparation so that the product can be used on the body or skin, particularly skincare products that bind to the epidermal estrogen receptor. The form product can be selected from the group consisting of gels, essences, lotions, sprays, essences for masks, or scalp tonics. The inventor has submitted Shatavari extract under the trademark name Rejeunir®. Its production method was patented under Thai Petty Patent No. 21300. The pharmacological effects were tested as follows.

Shatavari extract has a strong effect on stimulating the estrogen hormone. Shatavari extract concentration at 0.001 micrograms per milliliter (diluted 1,000 times) is 1.3032 times compared to the standard β-estradiol concentration at 1,000 micrograms per milliliter, as tested in breast cancer cells MCF7.

Shatavari extract is able to inhibit 5α-reductase. Its efficiency is 40.22% (10,000 micrograms per milliliter) compared to the standard finasteride, as tested in prostate cancer cells DU-145 at a non-cytotoxic concentration.

Shatavari extract is able to inhibit collagenase by 0.03 times that of vitamin C.

Shatavari extract is able to bind free-radical DPPH by 91.15%.

Shatavari extract is able to inhibit tyrosinase by 113.6%.

The Study of Estrogen Hormone Stimulation Activity

Breast cancer cells are the representatives of the study of estrogen receptor stimulation activity because breast cancer cells are responsible for estrogen hormone. According to the estrogen hormone stimulation activity study, Shatavari extract concentration of 0.001 micrograms per milliliter (diluted 1,000 times) has the highest % survival of breast cancer cells MCF7, at 139.70+10.34%. This is 1.3032 times higher than that of the standard β-estradiol, which the highest % survival of breast cancer cells MCF7 is 107.20+5.37% at a concentration of 1,000 micrograms per milliliter.

Figure 2:
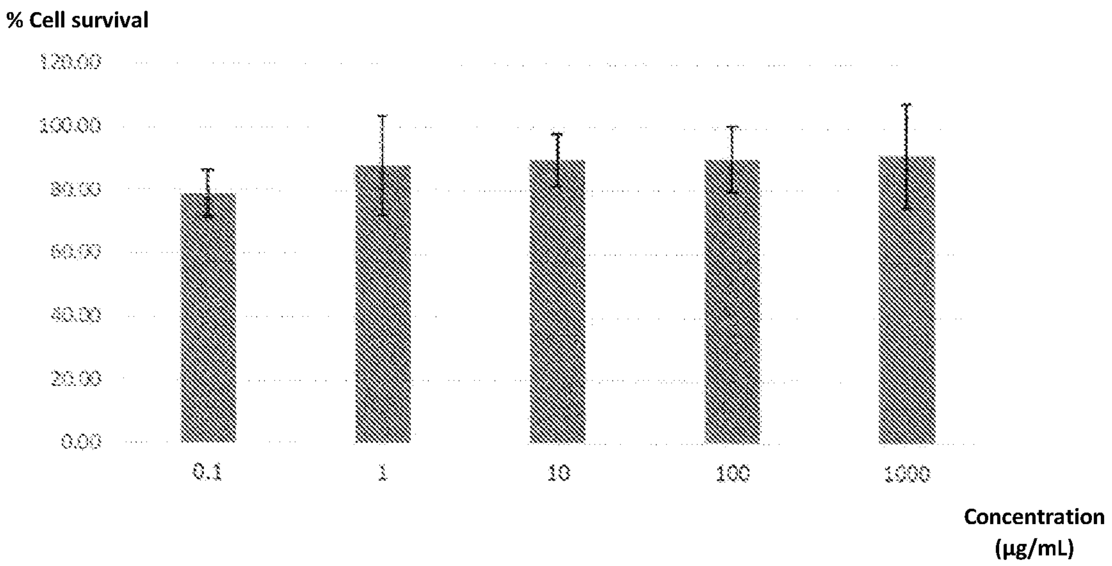
FIG. 2 shows % survival of breast cancer cells and β-estradiol.

The % survival of breast cancer cells MCF7 when treated with Shatavari extract at various concentrations is shown in Table 1 and FIG. 1, whereas the % survival of breast cancer cells MCF7 when treated with the standard β-estradiol at various concentrations is shown in Table 2 and FIG. 2.

TABLE 1

| Substance | % Survival of breast cancer cells MCF7 (means ± S.D.) (μg/mL) concentrations | | | | |
|---|---|---|---|---|---|
| | 0.0001 times | 0.001 times | 0.01 times | 0.1 times | 0 times |
| Shatavari extract | 129.61 ± 4.68 | 139.70 ± 10.34 | 120.51 ± 9.20 | 114.31 ± 4.84 | 112.41 ± 13.11 |

TABLE 2

| Substance | % survival of breast cancer cells MCF7 (means ± S.D.) (μg/mL) concentration | | | | |
|---|---|---|---|---|---|
| | 0.1 | 1 | 10 | 100 | 1,000 |
| β-estradiol | 92.14 ± 3.63 | 101.82 ± 8.51 | 98.84 ± 4.52 | 96.53 ± 5.61 | 107.20 ± 5.37 |

The Study of 5α-Reductase Inhibition Activity

Prostate cancer cells are the representatives of the study of 5α-reductase inhibition activity due to the production of 5α-reductase in prostate cancer cells. According to the study of 5α-reductase inhibition activity, Shatavari extract is non-cytotoxic to prostate cancer cells DU-145 at the highest concentration of 10,000 micrograms per milliliter, which is 87.17+1.92% cell survival. Standard finasteride is non-cytotoxic to prostate cancer cells at the highest concentration of 10 micrograms per milliliter, which is 96.78+1.20% cell survival.

Figure 3:
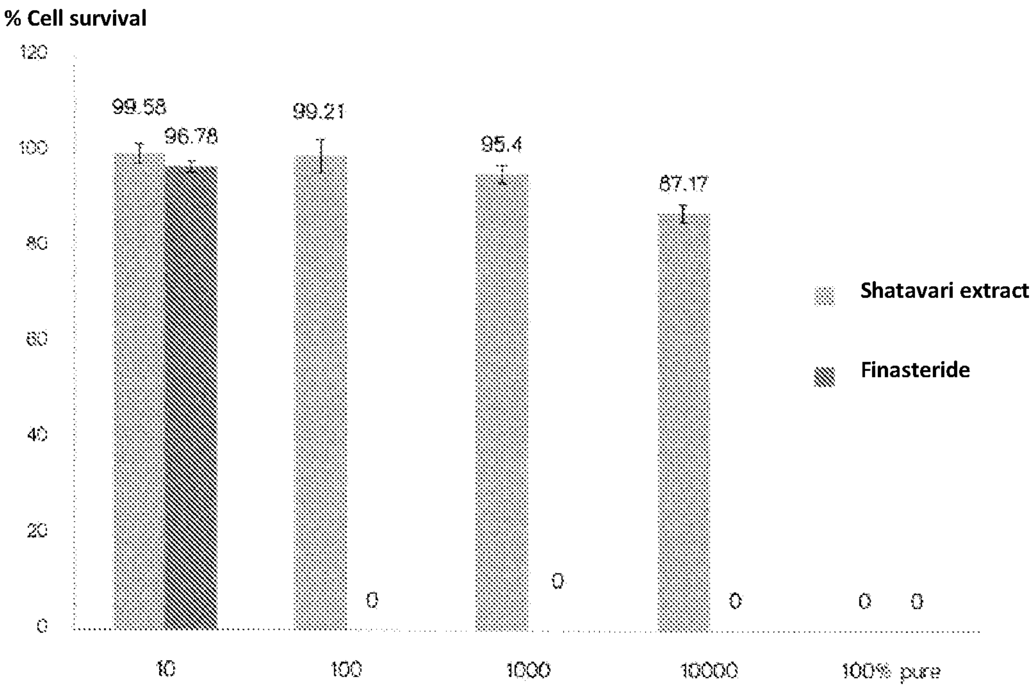
FIG. 3 shows % survival of prostate cancer cells, Shatavari extract, and finasteride.

The % survival of prostate cancer cells DU-145 when treated with Shatavari extract at various concentrations is shown in Table 3 and FIG. 3, whereas the % survival of prostate cancer cells DU-145 when treated with the standard finasteride at various concentrations is shown in Table 4 and FIG. 3.

TABLE 3

| Substance | % Survival of prostate cancer cells DU-145 (means ± S.D.) (μg/mL) concentration | | | | |
|---|---|---|---|---|---|
| | 10 | 100 | 1,000 | 10,000 | 100% |
| Shatavari extract | 99.58 ± 2.07 | 99.21 ± 3.48 | 95.40 ± 1.88 | 87.17 ± 1.92 | 0.00 |

TABLE 4

| Substance | % Survival of prostate cancer cells DU-145 (means ± S.D.) (μg/mL) concentration | | | | |
|---|---|---|---|---|---|
| | 0.01 | 0.1 | 1 | 10 | 100 |
| finasteride | 100.19 ± 1.16 | 99.75 ± 4.48 | 94.89 ± 2.85 | 96.78 ± 1.20 | 0 ± 0 |

Figure 4:
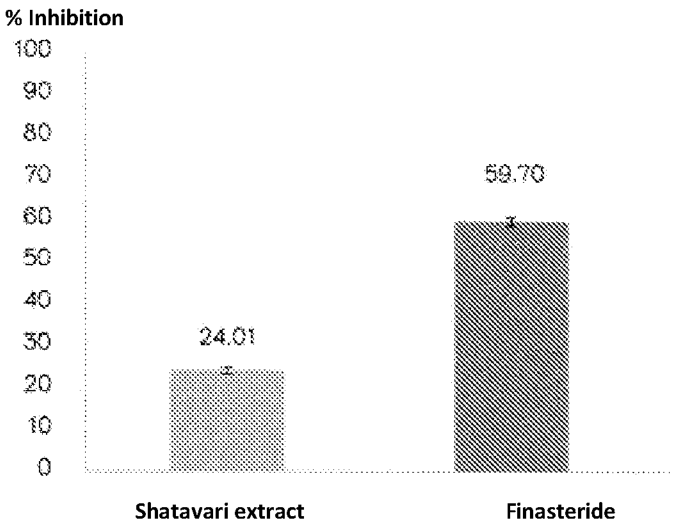
FIG. 4 shows % 5α-reductase inhibition of Shatavari extract and finasteride.
Figure 5:
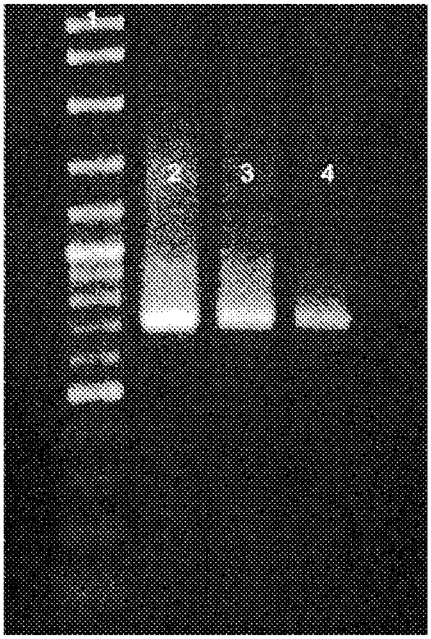
FIG. 5 shows agarose gel electrophoresis of the DNA of 5α-reductase enzyme from prostate cancer cells treated with Shatavari extract compared to finasteride.

The % 5α-reductase inhibition of Shatavari extract and the standard finasteride are shown in FIG. 4. The agarose gel electrophoresis of the DNA of the 5α-reductase enzyme from prostate cancer cells DU-145 when treated with Shatavari extract compared to standard finasteride is shown in FIG. 5. Lane 1 (left hand) is a known-length standard DNA (DNA ladder) of 100 bp. Lane 2 is a control DNA from prostate cancer cells that produces 5α-reductase as a 700-bp fragment. Lane 3 is from the Shatavari extract treatment. Lane 4 is from the finasteride treatment. The bands from lanes 3 and 4 are faded because they are able to inhibit 5α-reductase.

Figure 6:
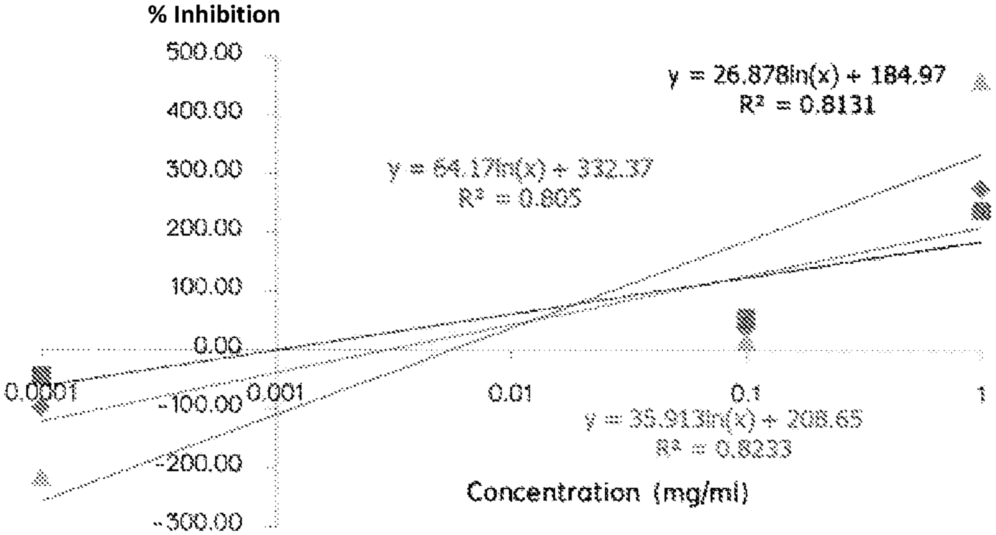
FIG. 6 shows % collagenase inhibition of vitamin C.
Figure 7:
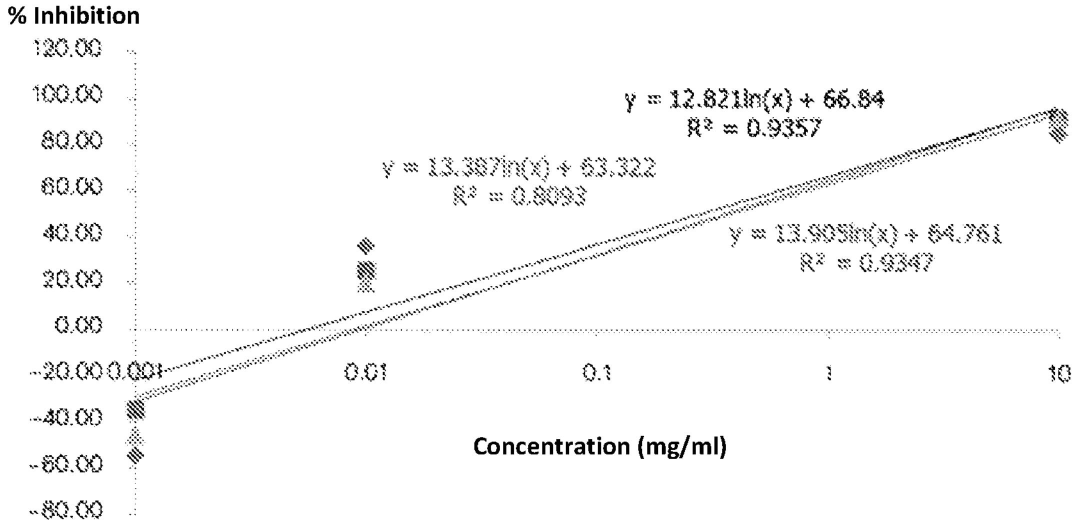
FIG. 7 shows % collagenase inhibition of Shatavari extract.

From the collagenase inhibition activity study, Shatavari extract is able to inhibit collagenase ($IC_{50}$ 0.33+0.05 milligrams per milliliter), as shown in FIG. 6. This is 0.03 times that of vitamin C ($IC_{50}$ 0.01+0.003 milligrams per milliliter), as shown in FIG. 7.

The vitamin C concentrations used in the collagenase inhibition activity study are 1, 0.1, 0.01, 0.001, and 0.0001 milligrams per milliliter. These are used in the collagenase inhibition activity study that use P-z peptide as a substrate. In a triplicate test, the $IC_{50}$ inhibiting collagenase is 0.01+0.003 milligrams per milliliter. Thus, the suitable vitamin C concentration in collagenase inhibition starts at 0.01 milligrams per milliliter, or 1% in the product. The most suitable vitamin C concentration in collagenase inhibition is 0.02 milligrams per milliliter, or 2% in the product. These are different from the amounts of vitamin C in common commercial cosmetic products, which use between 10 and 15% of vitamin C. The excessive use of vitamin C, far from the research data, not only wastes it but also makes it harder to formulate due to its solubility, acidity, and incompatibility with other ingredients. The inventors, thus, use vitamin C in the cosmetic product in particular amounts of 1-4% to achieve collagenase inhibition.

Free-Radical DPPH Binding Study

From the free-radical DPPH binding study, Shatavari extract has an $SC_{50}$ of 5.92+0.03 milligrams per milliliter. This is 0.0034 times that of vitamin C, of which $SC_{50}$ is 0.02+0.01 milligrams per milliliter. Also, the free-radical DPPH binding activity of non-diluted Shatavari extract is 91.15+0.97%.

The vitamin C concentrations used in the free-radical binding study are 100, 10, 1, 0.1, and 0.01 milligrams per milliliter. These are used in free-radical binding studies by the DPPH method and in free-radical nitric oxide binding using Griess reagent. In a triplicate test, the $IC_{50}$ values of free-radical binding by the DPPH method and free-radical nitric oxide binding are 0.02+0.01 and 0.84+0.02 milligrams per milliliter, respectively. Therefore, the suitable vitamin C concentration for free-radical binding starts at 0.02 milligrams per milliliter, or 2% in the product. The most suitable vitamin C concentration for free-radical binding is 0.04 milligrams per milliliter, or 4% in the product. These are different from the amounts of vitamin C in common commercial cosmetic products, which use between 10 and 15% of vitamin C. The excessive use of vitamin C, far from the research data, not only wastes it but also makes it harder to formulate due to its solubility, acidity, and incompatibility with other ingredients. The inventors, thus, use vitamin C in the cosmetic product in particular amounts of 1-4% for free-radical binding activity by the DPPH method, and for free-radical nitric oxide binding which causes anti-inflammation activity.

The Study of Tyrosinase Inhibition Activity

According to the study of tyrosinase inhibition activity, Shatavari extract has an $IC_{50}$ of 671.82+13.45 milligrams per milliliter. This is 0.00003 times that of kojic acid, of which $IC_{50}$ is 0.02+0.00 milligrams per milliliter. Also, the tyrosinase activity of non-diluted Shatavari extract is 113.60+0.09%.

In conclusion, Shatavari extract is very high effective in stimulating estrogen and high effective in inhibiting 5α-reductase. It is able to bind free-radical DPPH and moderately inhibit tyrosinase. Although it has low collagenase inhibition activity, this could be compensated for by adding vitamin C to the formulation. The final products cannot be tested for their pharmacological activities by the same method as the extract because the ingredients in the formulation interfere with optical absorption. Also, it is hard to interpret results as it becomes opaque when dissolved in cell culture media. Similarly, Shatavari extract in the anti-inflammation activity study with the nitric oxide method also becomes opaque, resulting in difficulty in interpretation.

BEST MODE FOR CARRYING OUT THE INVENTION

The best mode of invention is mentioned above in the detailed description section.

I claim:

1. A topical skincare composition consisting essentially of:

(a) 0.01-0.05 grams edetate disodium;

(b) 0.05-0.15 grams high molecular weight (MW) hyaluronic acid having a MW of greater than 1,800.00 Da;

(c) 0.05-0.20 grams medium molecular weight (MW) hyaluronic acid having a MW of 1,000,000 to 1,800,000 Da;

(d) 0.05-0.15 grams low molecular weight (MW) hyaluronic acid having a MW of 400,000 to less than 1,000,000 Da;

(e) 1.0-2.0 grams niacinamide;

(f) 1.0-2.0 grams Shatavari extract;

(g) 1.0 grams 2-phenoxyethanol;

(h) 0.18-0.56 grams carbomer;

(i) 1.0-4.0 grams L-ascorbic acid; and (j) water to 100 grams;

wherein the pH of the composition is adjusted to 5.5 with lactic acid;

wherein the Shatavari extract is obtained by co-solvent extraction with 95-97% ethanol and supercritical carbon dioxide; and wherein the composition optionally contains one or more additional ingredients selected from the group consisting of chelating agents, preservatives, pH-adjusting agents, gelling agents, cosmetic waxes and/or cosmetic oils, ceramides, emulsifiers, panthenol, and ferulic acid.

2. The topical skincare composition according to claim 1, wherein the composition contains said chelating agent, selected from the group consisting of ethylenediaminetetraacetic acid and ethylenediaminetetraacetic acid metal salts.

3. The topical skincare composition according to claim 1, wherein the composition contains said moisturizer, selected from the group consisting of hyaluronic acid S having a molecular weight of 100,000-400,000 Da, aloe vera gel, nutto gum, hydrolyzed protein, urea, amino acid, cholesterol, sodium L-pyroglutamate, sodium lactate, and propane-1,2,3-triol.

4. The topical skincare composition according to claim 1, wherein the composition contains said preservative, selected from the group consisting of benzyl alcohol; benzoic acid, and salts, and esters thereof; propionic acid, and salts thereof; salicylic acid, and salts thereof; sorbic acid, and salts thereof; o-phenylphenol, and salts thereof; 4-hydroxybenzoic acid, and methyl-, ethyl-, esters, and salts thereof; undec-10-enoic acid, and salts thereof; 3-(2-ethylhexyloxy) propane-1,2-diol; methyl paraben; propyl paraben; methyl parahydroxybenzoate; propyl parahydroxybenzoate; 2-bromo-2-nitropropane-1,3-diol; imidazolidinyl urea; methylcholroisothiazolinone; and ethylenediaminetetraacetic acid.

5. The topical skincare composition according to claim 1, wherein the composition contains said pH-adjusting agent, selected from the group consisting of triethanolamine, glycolic acid, and citric acid.

6. The topical skincare composition according to claim 1, wherein the composition contains said gelling agent, selected from the group consisting of xanthan gum, arabic gum, carrageenan, cellulose, synthetic cellulose, and okra mucilage.

7. The topical skincare composition according to claim 1, wherein the composition contains said cosmetic wax and/or cosmetic oil, selected from the group consisting of shea butter, mango wax, avocado wax, cupuacu butter, coconut wax, cacao wax, petrolatum, beeswax, soy wax, stearyl alcohol, cetyl alcohol, ceteareth-20, candelilla wax, cetearyl alcohol, carnauba wax, flaxseed oil, jojoba oil, rosehip oil, avocado oil, perilla oil, sacha inchi oil, coconut oil, caprylic or capric triglyceride, sunflower seed oil, castor oil, olive oil, carrot seed oil, argan oil, and tea seed oil.

8. The topical skincare composition according to claim 1, wherein the composition contains said ceramide, selected from the group consisting of ceramide 1, ceramide 1A, ceramide 2, ceramide 3, ceramide 6, ceramide 6 II, ceramide AP, ceramide AS, ceramide EOP, ceramide EOS, ceramide NP, and ceramide NS.

9. The topical skincare composition according to claim 1, wherein the composition contains said emulsifier, selected from the group consisting of propan-1,2,3-triol; hydrogenated lecithin; polyoxyethylene 20 sorbitan monooleate; polyoxyethylene 23 dodecanol; and triethanolamine.

10. A method for caring for scalp or skin, wherein said method comprises applying to the scalp or skin of a subject in need thereof a therapeutically effective amount of the composition according to claim 1;

wherein said composition is formulated as a gel, essence, lotion, spray, essence for a mask, or a scalp tonic; and wherein said composition binds to an epidermal estrogen receptor, inhibits tyrosinase, and/or inhibits 5α-reductase.

11. A skincare composition consisting of:

(a) 0.01-0.05 grams edetate disodium;

(b) 0.05-0.15 grams high molecular weight (MW) hyaluronic acid having a MW of greater than 1,800.00 Da;

(c) 0.05-0.20 grams medium molecular weight (MW) hyaluronic acid having a MW of 1,000,000 to 1,800,000 Da;

(d) 0.05-0.15 grams low molecular weight (MW) hyaluronic acid having a MW of 400,000 to less than 1,000,000 Da;

(e) 1.0-2.0 grams niacinamide;

(f) 1.0-2.0 grams Shatavari extract;

(g) 1.0 grams 2-phenoxyethanol;

(h) 0.18-0.56 grams carbomer;

(i) 1.0-4.0 grams L-ascorbic acid; and (j) water to 100 grams;

wherein the pH of the composition is adjusted to 5.5 with lactic acid;

wherein the Shatavari extract is obtained by co-solvent extraction with 95-97% ethanol and supercritical carbon dioxide; and wherein the composition optionally further contains one or more ingredients selected from the group consisting of:

(a) one or more moisturizers selected from the group consisting of hyaluronic acid S having a molecular weight of 100,000-400,000 Da, aloe vera gel, nutto gum, hydrolyzed protein, urea, amino acid, cholesterol, sodium L-pyroglutamate, sodium lactate, and propane-1,2,3-triol;

(b) one or more preservatives selected from the group consisting of benzyl alcohol; benzoic acid, and salts, and esters thereof; propionic acid, and salts thereof; salicylic acid, and salts thereof; sorbic acid, and salts thereof; o-phenylphenol, and salts thereof; 4-hydroxybenzoic acid, and methyl-, ethyl-, esters, and salts thereof; undec-10-enoic acid, and salts thereof; 3-(2-ethylhexyloxy)propane-1,2-diol; methyl paraben; propyl paraben; methyl parahydroxybenzoate; propyl parahydroxybenzoate; 2-bromo-2-nitropropane-1,3-diol; imidazolidinyl urea; methylcholroisothiazolinone; and ethylenediaminetetraacetic acid;

(c) an additional pH adjusting agent selected from the group consisting of triethanolamine, glycolic acid, and citric acid;

(d) one or more gelling agents selected from the group consisting of xanthan gum, arabic gum, carrageenan, cellulose, synthetic cellulose, and okra mucilage;

(e) one or more cosmetic waxes or cosmetic oils selected from the group consisting of shea butter, mango wax, avocado wax, cupuacu butter, coconut wax, cacao wax, petrolatum, beeswax, soy wax, stearyl alcohol, cetyl alcohol, ceteareth-20, candelilla wax, cetearyl alcohol, carnauba wax, flaxseed oil, jojoba oil, rosehip oil, avocado oil, perilla oil, sacha inchi oil, coconut oil, caprylic or capric triglyceride, sunflower seed oil, castor oil, olive oil, carrot seed oil, argan oil, and tea seed oil;

(f) one or more ceramides selected from the group consisting of ceramide 1, ceramide 1A, ceramide 2, ceramide 3, ceramide 6, ceramide 6 II, ceramide AP, ceramide AS, ceramide EOP, ceramide EOS, ceramide NP, and ceramide NS;

(g) one or more emulsifiers selected from the group consisting of propan-1,2,3-triol; hydrogenated lecithin; polyoxyethylene 20 sorbitan monooleate; polyoxyethylene 23 dodecanol; and triethanolamine; and (h) one or both of panthenol and ferulic acid.

12. A method for caring for scalp or skin, wherein said method comprises applying to the scalp or skin of a subject in need thereof a therapeutically effective amount of the composition according to claim 11;

wherein said composition is formulated as a gel, essence, lotion, spray, essence for a mask, or a scalp tonic; and wherein said composition binds to an epidermal estrogen receptor, inhibits tyrosinase, and/or inhibits 5α-reductase.

* * * * *